United States Patent
Kuhn (10) Patent No.: US 11,083,508 B2
(45) Date of Patent: Aug. 10, 2021

(54) DEFORMABLE CRANIAL BURR HOLE PLATE AND DEFORMATION INSTRUMENT THEREFOR

(71) Applicant: Stryker European Holdings I, LLC, Kalamazoo, MI (US)

(72) Inventor: Sven Martin Kuhn, Emmendingen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 268 days.

(21) Appl. No.: 16/056,803

(22) Filed: Aug. 7, 2018

(65) Prior Publication Data
US 2019/0046248 A1     Feb. 14, 2019

(30) Foreign Application Priority Data
Aug. 11, 2017   (EP) .................................... 17001379

(51) Int. Cl.
*A61B 17/80*   (2006.01)
*A61B 17/88*   (2006.01)
(Continued)

(52) U.S. Cl.
CPC .......... *A61B 17/809* (2013.01); *A61B 17/808* (2013.01); *A61B 17/8061* (2013.01); *A61B 17/8085* (2013.01); *A61B 17/8872* (2013.01); *A61B 17/688* (2013.01); *A61B 2017/00862* (2013.01); *A61B 2017/681* (2013.01)

(58) Field of Classification Search
CPC . A61B 17/809; A61B 17/826; A61B 17/8061; A61B 17/8085; A61B 17/808; A61B 7/8085; A61B 7/8872; A61B 17/686; A61B 17/688
See application file for complete search history.

(56) References Cited

U.S. PATENT DOCUMENTS

| | | |
|---|---|---|
| 4,328,813 A | 5/1982 | Ray |
| 5,503,164 A | 4/1996 | Friedman |

(Continued)

FOREIGN PATENT DOCUMENTS

| | | |
|---|---|---|
| EP | 1808140 A1 | 7/2007 |
| WO | 2011005788 A1 | 1/2011 |
| WO | 2016139576 A2 | 9/2016 |

OTHER PUBLICATIONS

Extended European Search Report including Written Opinion for Application No. EP17001379.1 dated Feb. 13, 2018.

*Primary Examiner* — Matthew J Lawson
(74) *Attorney, Agent, or Firm* — Lerner, David, Littenberg, Krumholz & Mentlik, LLP (57) ABSTRACT

A cranial burr hole plate is provided, the burr hole plate comprising a plate body and a plurality of spikes extending from the plate body. The spikes are configured to engage cranial bone, wherein the burr hole plate is deformable to enable movement of the spikes from a burr hole disengaging configuration to a burr hole engaging configuration upon deformation of the burr hole plate. Also provided is a deformation instrument for moving the spikes of a cranial burr hole plate into the burr hole engaging configuration is provided. Moreover, a cranial burr hole plating system is provided that comprises the cranial burr hole plate and the deformation instrument.

20 Claims, 7 Drawing Sheets

(51) Int. Cl.
*A61B 17/68* (2006.01)
*A61B 17/00* (2006.01)

(56) References Cited

U.S. PATENT DOCUMENTS

| | | | | |
|---|---|---|---|---|
| 5,707,373 | A * | 1/1998 | Sevrain | A61B 17/688 |
| | | | | 411/338 |
| 5,800,436 | A | 9/1998 | Lerch | |
| 6,126,663 | A * | 10/2000 | Hair | A61B 17/688 |
| | | | | 606/324 |
| 6,190,389 | B1 * | 2/2001 | Wellisz | A61B 17/688 |
| | | | | 606/281 |
| 6,511,482 | B1 | 1/2003 | Wellisz et al. | |
| 6,923,812 | B1 | 8/2005 | Wellisz | |
| 8,043,304 | B2 | 10/2011 | Barker | |
| 9,265,530 | B2 * | 2/2016 | Llas Vargas | A61B 17/8872 |
| 10,898,332 | B2 * | 1/2021 | Engstrand | A61B 17/8085 |
| 10,932,834 | B2 * | 3/2021 | Stupak | A61B 17/8085 |
| 2007/0083268 | A1 | 4/2007 | Teoh et al. | |
| 2012/0136397 | A1 | 5/2012 | Ralph et al. | |
| 2012/0283771 | A1 | 11/2012 | Ralph et al. | |
| 2017/0181840 | A1 * | 6/2017 | Floess | A61B 17/0642 |
| 2020/0360058 | A1 * | 11/2020 | Garcia | A61B 17/8061 |

\* cited by examiner

DEFORMABLE CRANIAL BURR HOLE PLATE AND DEFORMATION INSTRUMENT THEREFOR

CROSS-REFERENCE TO RELATED APPLICATIONS

The present application claims priority from EP Patent Application No. 17001379.1 filed Aug. 11, 2017, the disclosure of which is hereby incorporated herein by reference.

TECHNICAL FIELD

The present disclosure generally relates to surgical implants. In particular, a plate for covering a cranial burr hole and an instrument for fixing the implant to cranial bone are presented.

BACKGROUND OF THE INVENTION

Surgery for treating intracranial diseases often involves drilling a burr hole into the skull of a patient to obtain access to the intracranial region. In order to close the burr hole after the intracranial treatment, a plate covering the burr hole is then fixed to the cranial bone. To this end, conventional burr hole plates comprise screw openings to receive fixation screws that are screwed into the cranial bone.

Screwing the screws into the cranial bone is time-consuming and leads to longer surgery times. Furthermore, the utilized screws are expensive due to strict surgical requirements like biocompatibility and sterility.

There is a need for a burr hole plate that can easier be attached to cranial bone.

SUMMARY OF THE INVENTION

According to one aspect, a cranial burr hole plate is provided that comprises a plate body and a plurality of spikes extending from the plate body. The spikes are configured to engage cranial bone, wherein the burr hole plate is deformable to enable movement of the spikes from a burr hole disengaging configuration to a burr hole engaging configuration upon deformation of the burr hole plate.

At least part of the cranial burr hole plate may be formed from a biocompatible material like titanium, nitinol or titanium nitride. At least a portion of the cranial burr hole plate may be covered by a bio-compatible material. Moreover, at least a portion of the cranial burr hole plate may be bio-resorbable.

The plate body of the burr hole plate may be deformable. The plate body may have a burr hole covering portion. The burr hole covering portion may have one or more openings, or may not have any openings. The burr hole plate may be deformable by applying a force onto the burr hole covering portion. As such, at least the burr hole covering portion of the plate body may be deformable.

At least a part of the plate body, such as the burr hole covering portion, may be configured to assume one of a convex form with a positive curvature, a flat form with zero curvature and a concave form with a negative curvature when the spikes are in a burr hole disengaging configuration. As an example, the burr hole covering portion may be one of convex, flat or concave. The plate body may be deformable in such a manner that the plate body assumes a form with a decreased curvature when the spikes are in a burr hole engaging configuration. A decreased curvature may comprise deforming the plate body form from a convex form to a flat form, a convex form to a concave form, a flat form to a concave form, a convex form to a less convex form or a concave form to a more concave form.

The plate body may be essentially plastically deformable. The plate body may comprise areas with varying degrees of deformability. The plate body may be more deformable at radially outer areas compared to radially inner areas. The plate body may have areas with a reduced wall thickness that are configured to be more deformable. A plastically deformable plate body may, for example, be made from grade 2 or lower grade titanium.

The plate body may in another variant be essentially elastically deformable. An elastically deformable plate body may, for example, be made from grade 4 or higher grade titanium.

Furthermore, the elastically deformable plate body may have a bistable configuration with (at least) two stable states. The plate body may have different curvatures in the two stable states, as explained above. The plate body may be configured to bias the spikes into the burr hole engaging configuration when elastically deformed.

The tip of one or more of the spikes may have an essentially triangular shape with a wall thickness similar to that of the plate body. Therefore, such spikes may have an improved structural strength that supports maintaining the burr hole engaging configuration. Alternatively, the wall thickness of one or more of the spikes may decrease in a direction towards the tip. Therefore that tip may have a smaller contacting surface on the burr hole wall and exert a higher pressure. One or more of the spikes may have a plurality of tips. Moreover, one or more of the spikes may have a roughened surface at their sides facing cranial bone.

At least one of the spikes may be configured to contact a burr hole wall when the plurality of spikes is in the burr hole engaging configuration. The at least one of the spikes may be configured to contact at least one of an outer cortical layer, a diploe and an inner cortical layer of the burr hole wall.

The plate body may comprise a hub and spokes. The spokes may extend from the hub. The spokes may have the same length or different lengths.

The plate body may comprise a circumferential ring. The circumferential ring may be configured to contact a cranial bone surface. The circumferential ring may have an essentially circular, elliptical or polygonal form. The circumferential ring may have at least one recess extending from an outer rim of the ring towards the center. The circumferential ring may further be configured to support at least a part of the plurality of spikes. The spikes may extend from an inner rim of the circumferential ring. If the plate comprises a hub and spokes, the spokes may extend from the hub to the circumferential ring. Alternatively, or in addition, the spikes may extend from the spokes.

The plate body may comprise an alignment feature to align the plate body with a deformation instrument. The alignment feature may further comprise at least one opening in the plate body for inserting a portion of the deformation instrument into the opening. The alignment feature may be disposed at a geometric center of the plate body or spaced apart therefrom.

The cranial burr hole plate may be formed in one piece. The cranial burr hole plate may be formed from a metal sheet. The cranial burr hole plate may be formed by (e.g., laser) cutting and/or bending processes. The cranial burr hole plate may have a thickness of ca. 0.1 to 1.5 mm (e.g., of ca. 0.2 to 0.6 mm).

The plate body may have a bone facing side. In such a case the plurality of spikes may extend from the bone facing side of the plate body.

According to a second aspect, a deformation instrument for moving the spikes of a cranial burr hole plate into the burr hole engaging configuration is provided. The deformation instrument comprises a radially outer sleeve and a radially inner stamp disposed inside the radially outer sleeve and axially movable thereto. The stamp is configured to deform the burr hole plate upon application of an axial force on the stamp.

The stamp may comprise an actuation element on an end of the stamp. The stamp may be elastically biased away from the sleeve. Operation of the stamp may require overcoming the elastic bias.

The stamp may comprise a first stamp portion and a second stamp portion, wherein the first stamp portion is concentric to the second stamp portion. The first stamp portion may be configured to deform the plate body of the burr hole plate and the second stamp portion may be configured to deform the spikes of the burr hole plate.

The deformation instrument may comprise an alignment feature configured to engage the complementary alignment feature of the plate body. The alignment feature may be disposed on the stamp and/or the sleeve. The alignment feature may comprise a protrusion, such as a pin.

According to a third aspect, a cranial burr hole plating system is provided. The system comprises the cranial burr hole plate and the deformation instrument.

According to a fourth aspect, a method for closing a cranial burr hole is disclosed. The method comprises placing a deformable burr hole plate onto the burr hole, wherein the burr hole plate comprises a plate body and a plurality of spikes extending from the plate body. The method further comprises deforming the burr hole plate to move the spikes from a burr hole disengaging configuration to a burr hole engaging configuration in which the spikes engage cranial bone.

The step of deforming the burr hole plate may be performed by applying an axial force on the burr hole plate by a stamp of a deformation instrument.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description, exemplary embodiments of a deformable cranial burr hole plate and deformation instrument therefor will be explained with reference to the drawings. The same or similar reference numerals will be used to denote the same or similar structural features.

Figure 1A:
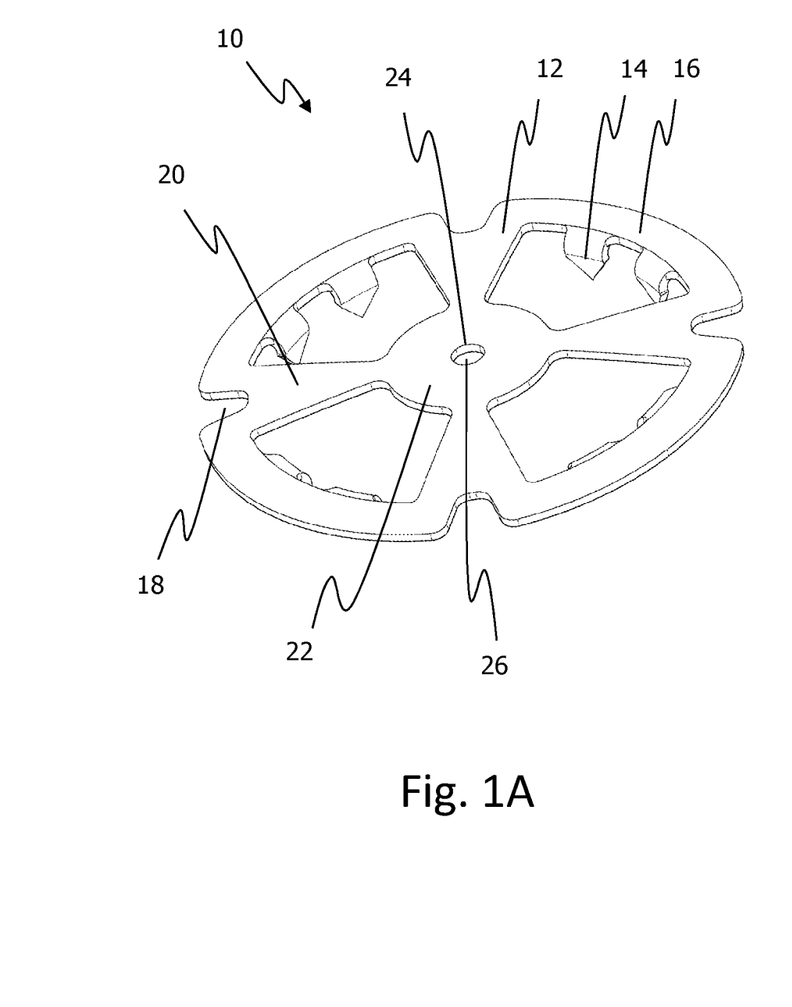
FIG. 1A shows a perspective top view of an embodiment of a cranial burr hole plate.

FIG. 1A shows a perspective top view of an embodiment of a cranial burr hole plate 10. The burr hole plate 10 comprises a plate body 12 and eight spikes 14 extending from the plate body 12. It will be appreciated that a different number of spikes could be provided (e.g., three to twelve). In the state of the burr hole plate 10 illustrated in FIG. 1A, the spikes 14 are in a burr hole disengaging configuration.

The plate body 12 comprises a circumferential ring 16 with four recesses 18. The recesses 18 extend from an outer rim of the ring 16 towards its center and enable gripping of the cranial burr hole plate 10 in a torque proof manner. It will be appreciated that a different number of recesses could be provided (e.g., two to eight).

The plate body 10 further comprises four spokes 20 that extend from the circumferential ring 16 radially inwardly to a central hub 22. Therefore, the spokes 20 mechanically connect the circumferential ring 16 with the hub 22.

The hub 22 comprises an alignment feature 24 in the form of a circular opening 26. The opening 26 is configured to receive a part of a deformation instrument. The opening 26 limits radial movement of the deforming instruments and aligns the deforming instrument with the burr hole plate 10. Alternatively or additionally, the alignment feature 24 can be located at another location of the burr hole plate 10.

The spokes 20 define openings therebetween that allow (e.g., visual) access to underlying cranial tissue and to the spikes 14. Alternatively, the plate body 10 may comprise no openings for an increased structural strength and better protection of the underlying cranial tissue.

The plate body 12 has a convex form. Therefore, the hub 22 extends in a direction away from the cranial burr hole 32.

Figure 1B:
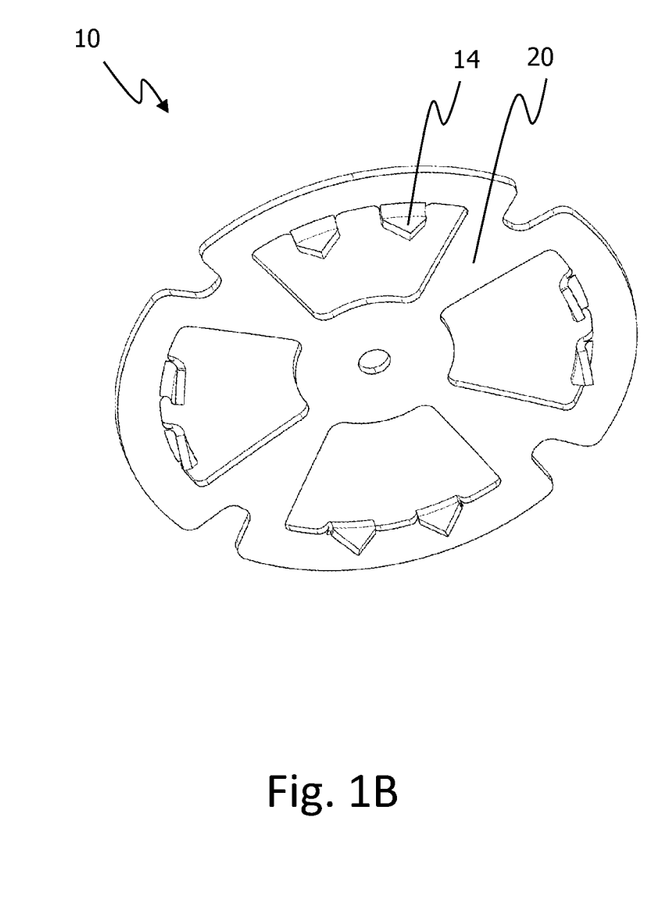
FIG. 1B shows a perspective bottom view of the embodiment of the cranial burr hole plate of FIG. 1A.

FIG. 1B shows a perspective bottom view of the embodiment of the cranial burr hole plate 10 with the spikes 14 still in a burr hole disengaging configuration. As illustrated in FIG. 1B, the eight spikes 14 are combined to four pairs of two spikes 14. The spikes 14 may be combined to groups of different numbers. Alternatively, the spikes 14 may be angularly evenly distributed.

Each spike 14 has a pointed tip that, when biased against the cranial bone material, resists movement of the spike 14 relative to the cranial bone material. This can be achieved by at least one of friction and forming a dent in the cranial bone material by the tip of the spike 14.

The burr hole plate 10 is formed in one piece from a metal sheet. The metal sheet may be made from grade 2 titanium so that the burr hole plate 10 is substantially plastically deformable. In other embodiments, the burr hole plate 10 may be made from grade 4 titanium and have elastically deformable properties. In particular, the burr hole plate 10 may have a bistable configuration such that the plate body 10 may have different curvatures in the two stable states, as explained above.

In the embodiment of FIGS. 1A and 1B, there are no spikes 14 disposed at the spokes 20. Alternatively, or in addition, spikes could extend from the spokes 20. The spikes could also be separate elements that are attached to the plate body 12 (e.g. by clamping or welding).

Figure 2:
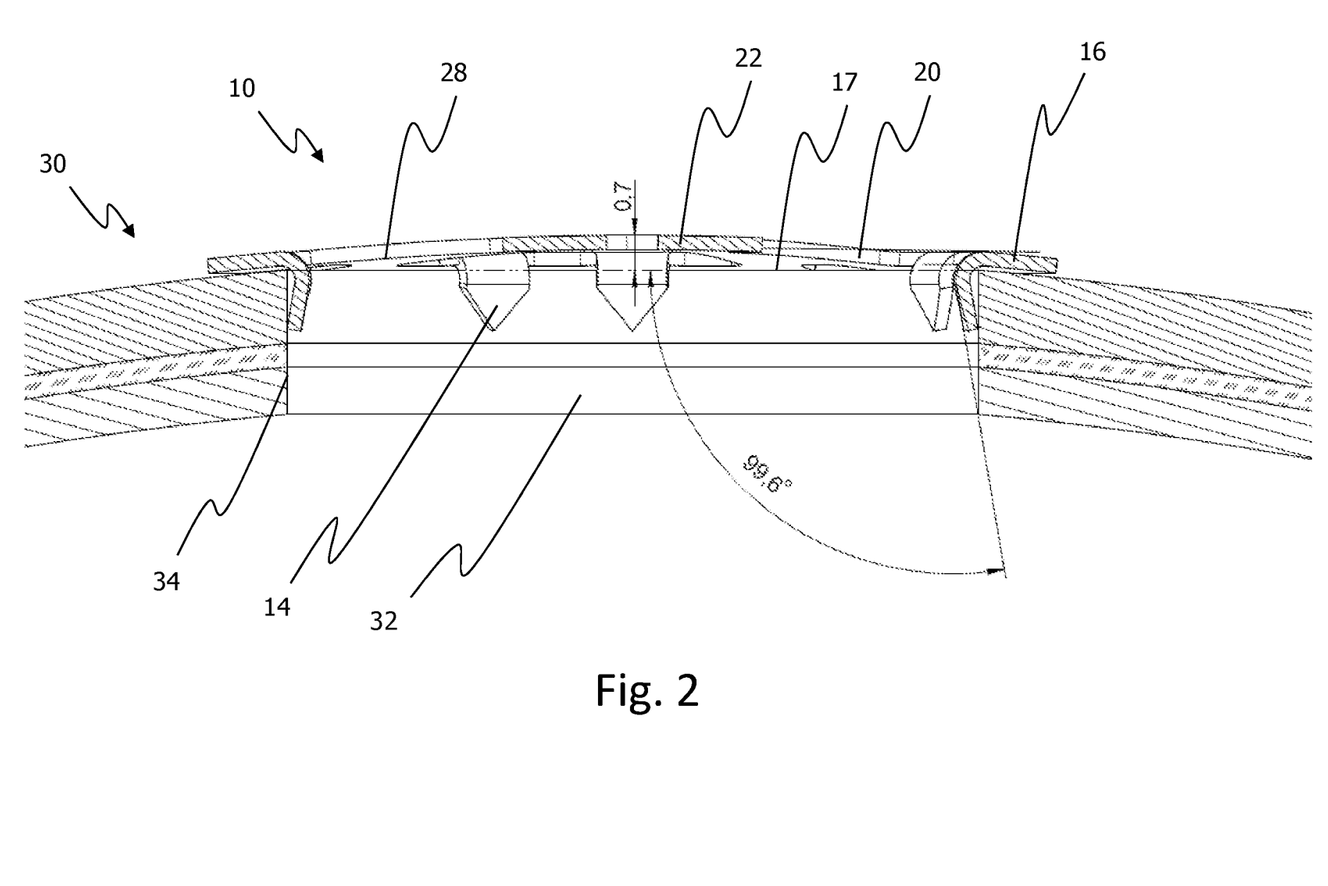
FIG. 2 shows a cross-sectional view of the embodiment of the cranial burr hole plate of FIGS. 1A and 1B in a burr hole disengaging configuration disposed in a burr hole.

FIG. 2 shows a cross-sectional view of the embodiment of the cranial burr hole plate 10 of FIGS. 1A and 1B in a burr hole disengaging state and disposed in a burr hole 32. The burr hole 32 is disposed in the cranial bone material of a skull 30 and has an essentially cylindrical shape with a burr hole wall 34.

The plate body 12 of the burr hole plate 10 has a bone facing side 28. The spikes 14 extend from the bone facing side 28 towards the burr hole 32. The bone facing side 28 of the circumferential ring 16 is configured to contact an outer surface of the skull 30 in the region adjacent to the burr hole 32.

When the cranial burr hole plate 10 is in its burr hole disengaging configuration, the plate body 12 has a convex shape, wherein the hub 22 extends out of a base plane 17 in a direction away from the cranial burr hole 32. The base plane 17 is defined by the upper rim of the burr hole 32.

In the embodiment illustrated in FIG. 2, the hub 22 is spaced from the base plane 17 by ca. 0.7 mm. The hub may generally be spaced from the base plane 17 by a different distance between 0.2 mm to 3.0 mm.

Alternatively, the plate body 12 may have a flat shape and extend within the base plane when the spikes 14 are in the burr hole disengaging configuration. As a further alternative, the plate body 12 may have a concave shape, wherein the hub 22 is spaced from the base plane 17 towards the inside of the cranium.

As illustrated in FIG. 2, the spikes 14 extend relative to the base plane 17 at an angle of 99.6° in their burr hole disengaging configuration. In general the spikes 14 may extend relative to the base plane 17 at an angle of ca. 85° to 115° (e.g., ca. 95° to ca. 105°). The angle may vary for each spike 14.

Figure 3:
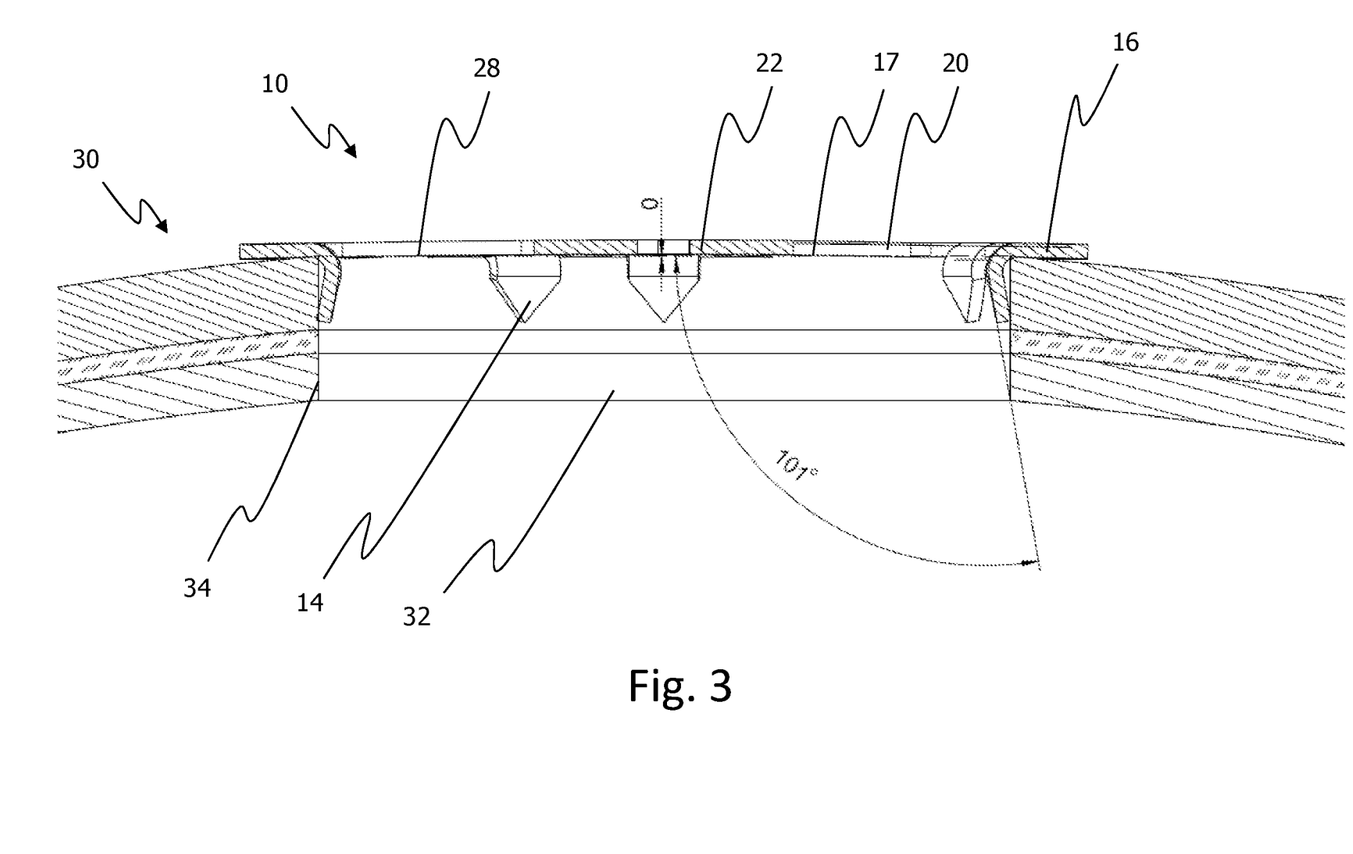
FIG. 3 shows a cross-sectional view of the embodiment of the cranial burr hole plate of FIGS. 1A and 1B in a burr hole engaging configuration disposed in a burr hole.

FIG. 3 shows a cross-sectional view of the cranial burr hole plate 10 in a burr hole engaging state and disposed in a burr hole 32. Compared to the burr hole plate 10 shown in FIG. 2, the burr hole plate 10 has been elastically deformed from a convex shape to a substantially flat shape, so that the hub 22 is disposed in the base plane 17. The deformation has been obtained by applying a force on the central region of the burr hole plate 10 (e.g., in the region of the hub 22 and an adjacent region of the spokes 20).

For the burr hole engaging configuration, the angle of the extension of the spikes 14 relative to the base plane 17 increased compared to the burr hole disengaging configuration illustrated in FIG. 2. Specifically, the angle of extension is increased to 101°, so that the spikes 14 (more firmly) contact the wall 34 of the burr hole 32. Generally, the angle of extension of the spikes 14 may increase by 0.5° to 4° relative to their burr hole disengaging configuration.

Due to a deformation, the radially outer rim of the circumferential ring 16 rotates away from the skull 30. The spokes 20 at the radially inner rim thus rotate towards the skull 30. Therefore, the spikes 14 also rotate (further) towards wall 34 to assume their burr hole engaging configuration.

The deformation is not limited to the example illustrated in FIGS. 2 and 3. In general, the spikes 14 will be in a burr hole engaging configuration when the plate body 10 assumes a form with a decreased curvature compared to a form of the plate body 10 when the spikes 14 are in their burr hole disengaging configuration.

The spikes 14 may contact different layers 36 of the cranial bone material in their burr hole engaging configuration as will now be discussed in regard to FIGS. 4A and 4B.

Figure 4A:
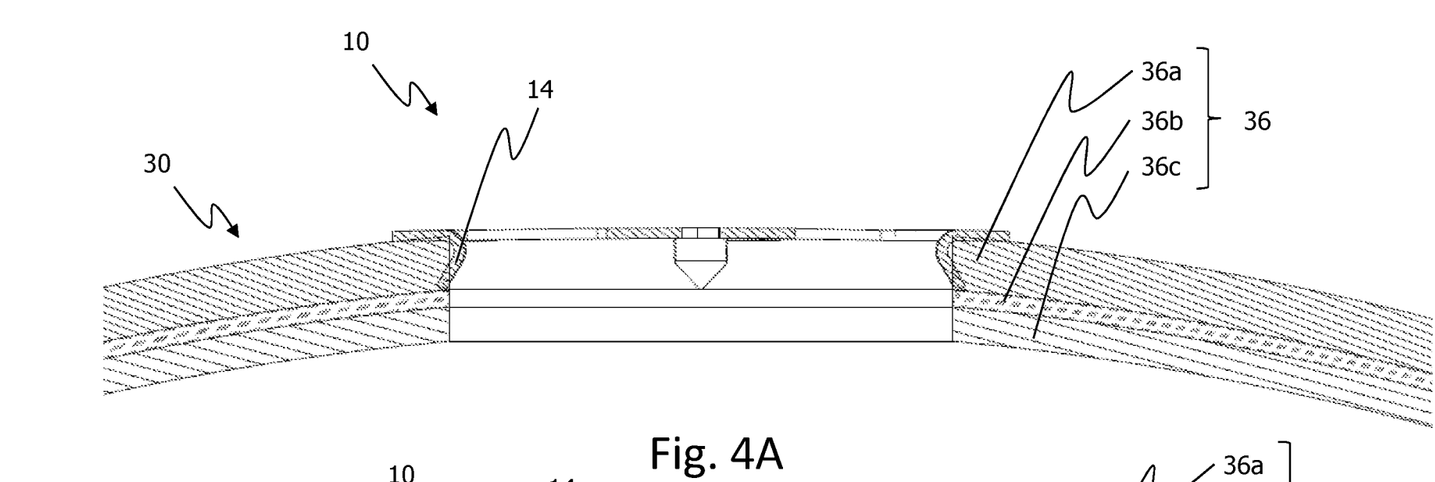
FIG. 4A shows a cross-sectional view of the embodiment of the cranial burr hole plate of FIGS. 1A and 1B engaging an outer cortical layer.
Figure 4B:
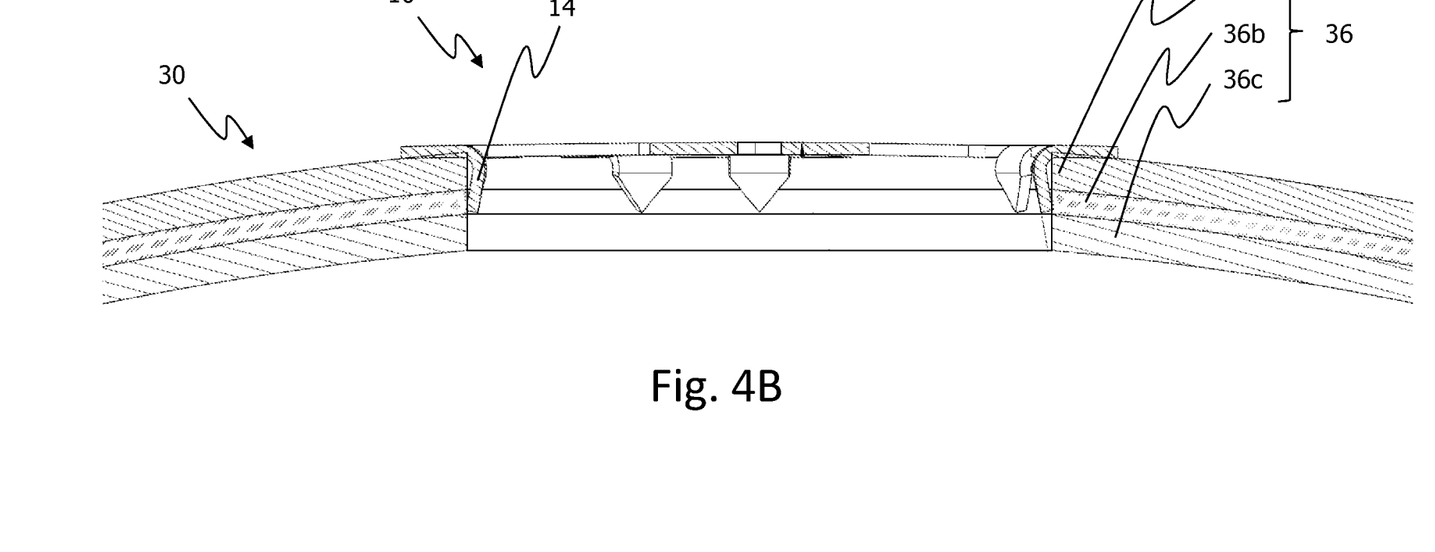
FIG. 4B shows a cross-sectional view of the embodiment of the cranial burr hole plate of FIGS. 1A and 1B engaging a diploe layer.

FIG. 4A shows a cross-sectional view of the cranial burr hole plate 10 engaging an outer cortical layer 36a. FIG. 4B shows a cross-sectional view of the cranial burr hole plate 10 engaging a diploe layer 36b. The cranial burr hole plate 10 can also be configured to contact an inner cortical layer 36c. The particular bone layer to be contacted by a particular spike 14 can be determined by a length and/or angle of that spike 14. A spike 14 can also be configured to comprise a plurality of tips, which can contact the same or different cortical layers 36. Two spikes can each be configured to contact different cortical layers 36. This advantageously allows asymmetrical designs that take into account varying thicknesses of the cortical layers 36.

Figure 5A:
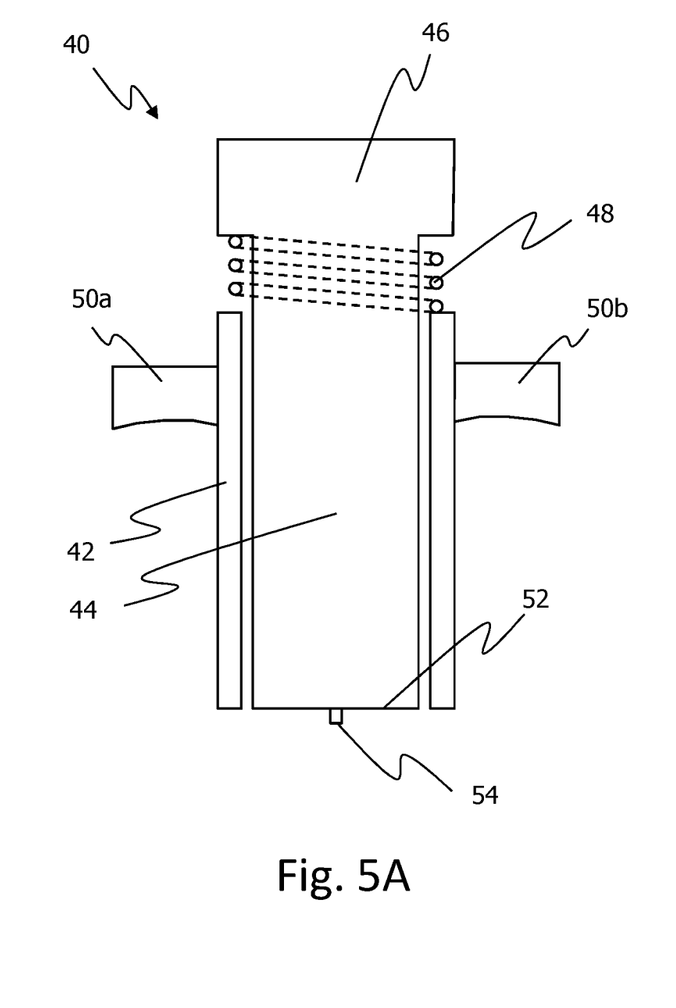
FIG. 5A shows a cross-sectional view of a first embodiment of a deformation instrument.

FIG. 5A shows a cross-sectional view of an embodiment of a deformation instrument 40. The deformation instrument may be employed to deform the cranial burr hole plate 10 from the state shown in FIG. 2 to the state shown in FIG. 3. Alternatively, this deformation may also be achieved by another type of instrument or by pressing on the cranial burr hole plate 10 with a finger of the surgeon's hand.

The deformation instrument 40 of FIG. 5A comprises a radially outer sleeve 42 and a radially inner stamp 44. The radially inner stamp 44 is disposed inside the radially outer sleeve 42 and is axially movable thereto. The stamp 44 comprises an actuation element 46 with a radial extension that exceeds an inner diameter of the sleeve 42 and therefore prevents movement of the actuation element 46 into the sleeve 42. The deformation instrument 40 further comprises a spring 48 that axially biases the stamp 44 relative to the sleeve 42. The actuation instrument 40 further comprises two handles 50a, 50b for being engaged by the surgeon's fingers.

The actuation element 46 and the handles 50a, 50b enable an application of a force that moves the stamp 44 axially relative to the sleeve 42 against the bias of the spring 48. In one exemplary embodiment, the surgeon presses with a thumb or palm onto the actuation element 46 and pulls on both handles 50a, 50b with an index finger and a middle finger to control axial movement of the stamp 44 relative to the sleeve 42. The stamp 44 has a bottom surface 52 configured to transfer the force that is applied on the deformation instrument 40 to the cranial burr hole plate 10.

Figure 5B:
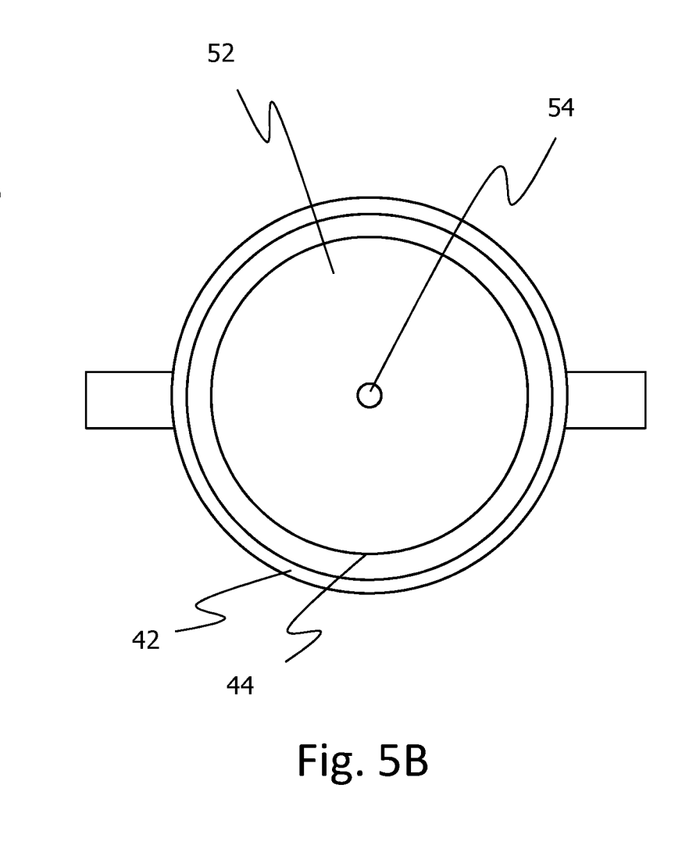
FIG. 5B shows a perspective view of a bottom surface of the first embodiment of the deformation instrument in FIG. 5A.

The stamp 44 further comprises an optional alignment feature 54 extending from the bottom surface 52. The alignment feature 54 comprises a pin or similar structure. The alignment feature 54 of the stamp 44 is configured to engage the complementary alignment feature 24 (see the corresponding opening in the hub 22 illustrated in FIG. 1A) of the plate body 12 of the burr hole plate 10. The alignment feature 52 prevents or limits radial movement of the stamp 44 relative to the burr hole plate 10, particularly when applying a force onto the stamp 44.

During cranial surgery, the surgeon operates the deformation instrument 40 as follows.

The surgeon first places the cranial burr hole plate 10 onto a burr hole 32 as generally shown in FIG. 2 and places the deformation instrument 60 on top of the burr hole plate 10.

At this time, the surgeon inserts the pin of the alignment element 54 into the opening of the alignment element 24 of the hub 22.

Alternatively, the deformation instrument 40 may comprise an attachment feature (not shown) that enables temporary attachment of the burr hole plate 10 to the deformation instrument 40. Once the burr hole plate 10 has been picked up by the attachment feature of the deformation instrument 40, the surgeon, using the deformation instrument 40, positions the burr hole plate 10 onto the burr hole 32.

Initially, the sleeve 42 rests on the circumferential ring 16 and therefore does not exert any significant deformation force onto the plate body 12. The surgeon then grips the handles 50*a*, 50*b* with the index and middle finger and pushes with the thumb or palm onto the actuation element 46. The stamp 44 transfers the applied force onto the plate body 12, wherein the plate body 12 is deformed in such a way that it assumes a form with a decreased curvature (see FIG. 3, the deformation instrument 40 has again been omitted).

As explained above, due to the resulting deformation, the spikes 14 move from a burr hole disengaging configuration to a burr hole engaging configuration. After having deformed the plate body 12, the surgeon stops applying a force onto the actuation element 46, and the spring 48 biases the stamp 44 away from the body plate 12. Then, the surgeon removes the deformation instrument 40 from the burr hole plate 10.

Figure 6A:
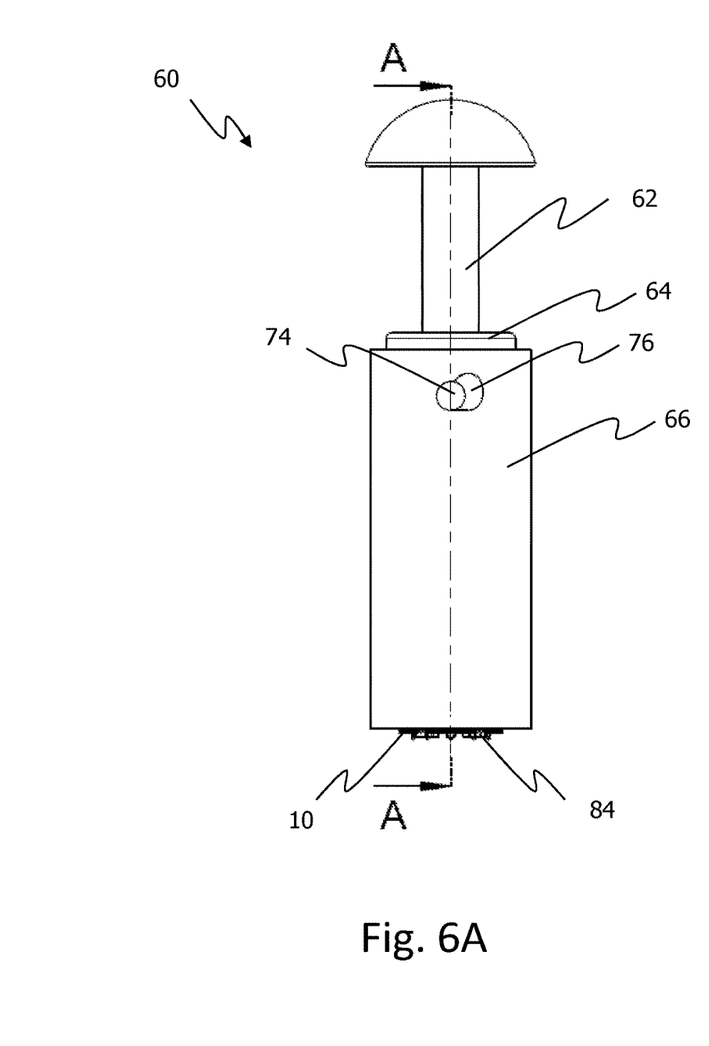
FIG. 6A shows a side view of a second embodiment of a deformation instrument.
Figure 6B:
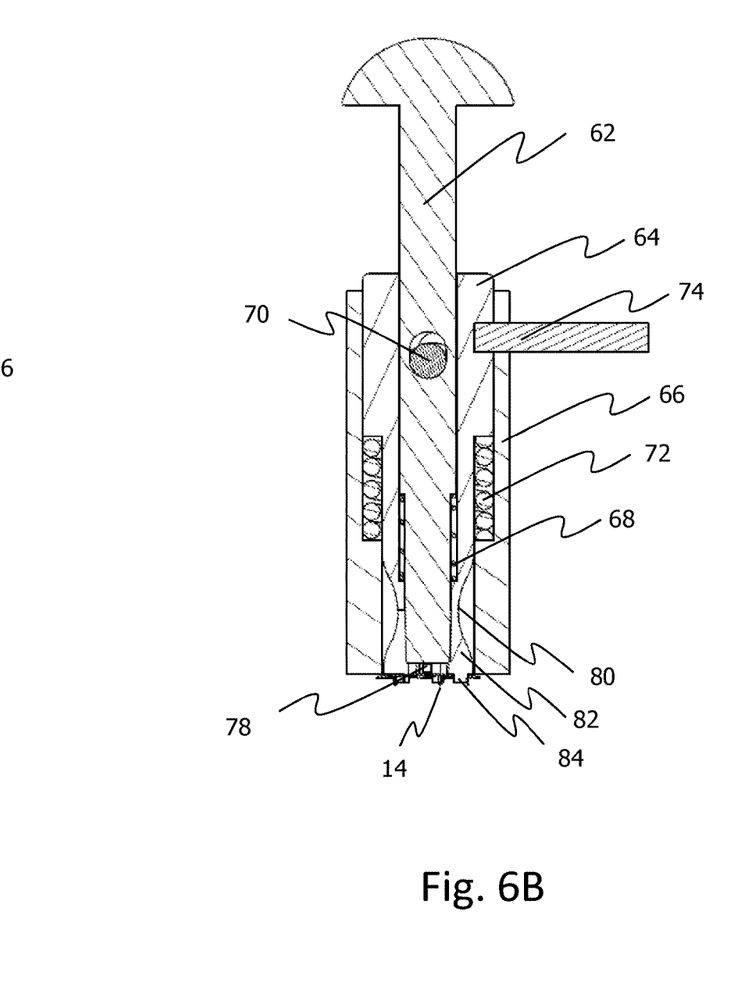
FIG. 6B shows a cross-sectional view of the second embodiment of a deformation instrument along the line A-A in FIG. 6A.
Figure 6C:
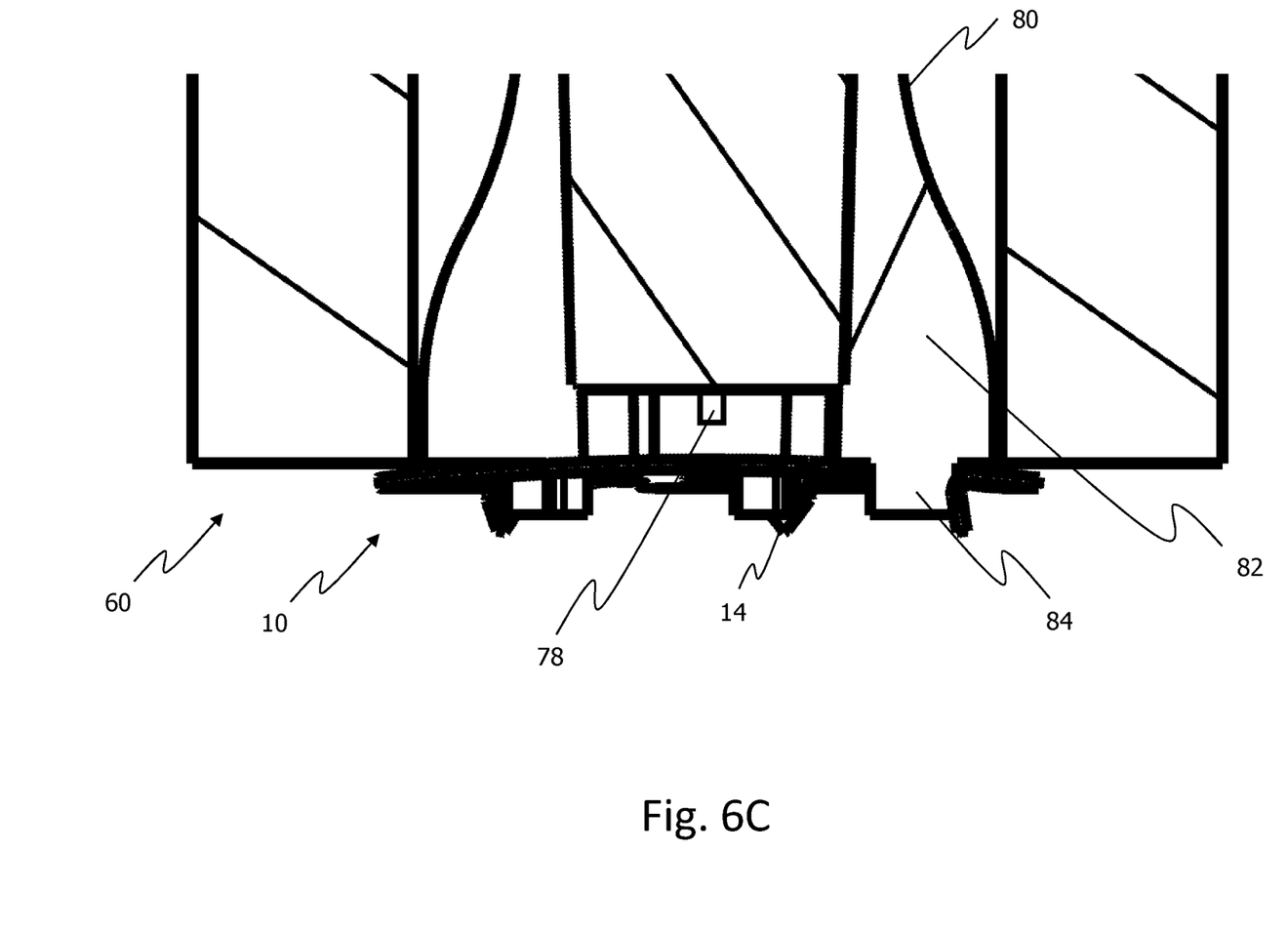
FIG. 6C shows an enlarged cross-sectional view of the bottom of the second embodiment of a deformation instrument.

FIG. 6A shows a side view of a second embodiment of a deformation instrument 60 and FIG. 6B shows a cross-sectional view of the second embodiment of the deformation instrument 60 along the line A-A in FIG. 6A. FIG. 6C shows an enlarged cross-sectional view of the bottom of the deformation instrument 60. The main differences between the second embodiment and the first embodiment of the deformation instrument are a stamp that comprises two concentric stamp portions and stamp protrusions extending from stamp fingers of the stamp.

The deformation instrument 60 illustrated in FIGS. 6A to 6C comprises a first stamp portion 62, a second stamp portion 64 and an outer sleeve 66. The first stamp portion 62 is disposed in a cylindrical opening of the second stamp portion 64 and is axially movable thereto, wherein the first stamp portion 62 is axially biased against the second stamp portion 64 by means of a first spring 68. A stopping bar 70 extends through a vertically elongated opening in the first stamp portion 62 and is mechanically connected with the second stamp portion 64, but not with the outer sleeve 66. The stopping bar 70 limits axial movement of the first stamp portion 62 relative to the second stamp portion 64 and prevents unintended separation of both stamp portions 62, 64.

The first stamp portion 62 and the second stamp portion 64 are disposed inside the outer sleeve 66. The second stamp portion 64 is axially movable relative to the outer sleeve 66 and axially biased relative thereto by means of a second spring 72. The second spring 72 may have a larger spring constant than the first spring 68. The second stamp portion 64 is rotationally movable relative to the outer sleeve 66.

The second stamp portion 64 comprises a handle 74 that allows the surgeon to apply a torque to the second stamp portion 64. To that end, the sleeve 66 comprises a handle opening 76. The handle 74 extends through that handle opening 76. The handle opening 76 has an L-shape with horizontally and vertically extending portions. The horizontal extension of the handle opening 76 enables movement of the handle 74 during rotational movement of the second stamp portion 64 relative to the sleeve 66. The vertical extension of the handle opening 76 enables movement of the handle 74 during axial movement of the second stamp portion 64 relative to the sleeve 66.

The first stamp portion 62 further comprises an alignment feature 78 extending from the bottom of the first stamp 62. The alignment feature 78 comprises a pin or similar structure. The alignment feature 78 of the first stamp portion 62 is configured to engage the complementary alignment feature 24 (see the corresponding opening in the hub 22 illustrated in FIG. 1A) of the plate body 12 of the burr hole plate 10. The alignment feature 78 prevents or limits radial movement of the first stamp portion 62 relative to the burr hole plate 10, particularly when applying a force onto the first stamp portion 62.

The second stamp portion 64 comprises a plurality of stamp fingers 80 axially extending downwards with a stamp protrusion 84 extending from each lower end of a stamp finger 80. The stamp fingers 80 are circumferentially separated by slits (not shown) and biased radially outwards against the outer sleeve 66. When the second stamp portion 64 is moved axially downwards, the stamp fingers 80 slide along the outer sleeve 66. When a tapering 82 of the second stamp portion 64 reaches the bottom of the outer sleeve 66, the stamp fingers 80 as well as the stamp protrusions 84 move radially outwards due to the radial bias of the stamp fingers 80.

The stamp protrusions 84 are configured to engage the spikes 14 (see the corresponding spikes 14 illustrated in FIG. 1A) from a radially inner side. When the stamp protrusions 84 engage the spikes 14 of the burr hole plate 10 and move radially outwards, the bias of the stamp fingers 80 exerts a radial force onto the spikes 14, which pushes the spikes 14 (further) outwards. For this purpose the surface of the stamp protrusions 84 may be inclined at the spike 14 engaging side in such a way that an axial downward movement of the stamp protrusions 84 pushes the spikes 14 that contact the inclined surface of the stamp protrusions 84 radially outwards.

During cranial surgery, the surgeon operates the deformation instrument 60 as follows.

The surgeon first places the cranial burr hole plate 10 onto a burr hole 32 as generally shown in FIG. 2 and places the deformation instrument 60 on top of the burr hole plate 10. When doing this, the surgeon inserts the pin of the alignment feature 78 into the opening of the alignment element 24 of the hub 22. Moreover, when placing the deformation instrument 60 on top of the burr hole plate 10, the surgeon moves the stamp protrusions 84 through the openings of the burr hole plate until they engage the radially inner side of the spikes 14.

Alternatively, the deformation instrument 60 may comprise an attachment feature (not shown) that enables temporary attachment of the burr hole plate 10 onto the deformation instrument 60. Once the burr hole plate 10 has been picked up via the attachment feature, the surgeon, using the deformation instrument 60, positions the burr hole plate 10 in the burr hole 32.

Then the surgeon applies an axial force onto the top of the first stamp portion 62 against the bias of the first spring 68. The first stamp portion 62 contacts the burr hole plate 10, wherein the force applied by the surgeon deforms the burr hole plate 10 in such a way that it assumes a form with a decreased curvature. As explained above, due to the resulting deformation, the spikes 14 move from a burr hole disengaging configuration to a burr hole engaging configuration. In the following step, the spikes 14 are further bent radially outwards in order to improve the engagement between the spikes 14 and the cranial burr hole 32.

The handle 74 is disposed in the vertically elongated portion of the handle opening 76 and therefore does not block axial movement of the second stamp portion 64 relative to the sleeve 66. The first stamp portion 62 is axially moved to such an extent that the vertical opening of the first stamp portion 62 now contacts the top of the stopping bar 70. Therefore, the axial force applied by the surgeon onto the first stamp portion 62 is also applied to the second stamp portion 64. In an alternative embodiment, the first stamp portion 62 contacts the second stamp portion 64 due to a completely compressed first spring 68.

The force applied by the surgeon axially moves the second stamp portion 64 relative to the outer sleeve 66 until the tapering 82 of the second stamp portion 64 reaches the bottom side of the outer sleeve 66. Alternatively, the surgeon may apply an axial force onto the outer sleeve 66 in an upwards direction. To this end, the handle opening 76 may comprise another vertical extension that extends downwards. The handle opening 76 may, for example, have the shape of a capital T that is rotated 90° to the side. The second vertical extension of the handle opening 74 may provide an increased range for axial movement of the outer sleeve 66 relative to the second stamp portion 64 and therefore also relative to the tapering 82.

As explained above, due to the tapering 82 and the bias of the second stamp portion 64, the stamp fingers 80 exert a force radially against the spikes 14 instead of the outer sleeve 66 when the tapering 82 has been moved out of the sleeve 66. Due to this force, the spikes 14 are pushed further into the cranial bone, which improves the engagement of the burr hole plate 10 with the cranial burr hole 32. The deformation of the burr hole plate 10 is now completed.

At this point the surgeon still applies a force onto the first stamp portion 62. Therefore, the surgeon rotates the second stamp portion 64 relative to the outer sleeve 66 by horizontally rotating the handle 74 into the horizontally elongated portion of the handle opening 76. In this handle configuration the handle opening 76 is configured to block axial movement of the handle 74 as well as the second stamp portion 64 relative to the outer sleeve 66. Therefore the surgeon can stop applying axial force onto the first stamp portion 62, wherein the first stamp portion 62 is moved upward by means of the first spring 68, removing the alignment feature 78 from the burr hole plate 10. The rotation of the second stamp portion 64 also rotates the stamp protrusions 84 relative to the spikes 14 in such a way that the stamp protrusions 84 do no longer engage the spikes 14. Therefore, the surgeon can remove the deformation instrument 60 from the burr hole plate 10.

Once the deformation instrument 60 has been removed from the burr hole plate 10, the surgeon moves the handle 74 back into the vertically elongated portion of the handle opening 76 allowing the second spring 72 to axially decompress. The deformation instrument 60 is now back in the initial configuration and can be used for the deformation of another burr hole plate 10.

As has become apparent from the above, the burr hole plate 10 can easily be implanted without the need to use additional fixation elements such as bone screws, although it might be contemplated to pre-fix the burr hole plate 10 as explained above and additionally use one or more screws for a final fixation of the burr hole plate 10. In such a case the burr hole plate may additionally comprise one or more screw holes, for example in the region of the circumferential ring 16.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A cranial plate, comprising:
   a plate body including a circumferential ring, a central hub, and a plurality of spokes extending radially inward from the circumferential ring to the central hub; and
   a plurality of spikes extending from the plate body, the spikes configured to engage cranial bone,
   wherein the plate is deformable to enable movement of the spikes from a disengaging configuration to an engaging configuration upon deformation of the plate, and
   wherein when the plate is deformed the plurality of spikes are bent away from the central hub and toward the circumferential ring to move the plurality of spikes from the disengaging configuration to the engaging configuration.

2. The cranial plate according to claim 1, wherein the plate body has a burr hole covering portion and the plate is deformable by applying a downward force onto the burr hole covering portion.

3. The cranial plate according to claim 1, wherein at least a portion of the plate body is configured to assume one of a convex form with a positive curvature, a flat form with zero curvature and a concave form with a negative curvature when the spikes are in a disengaging configuration, and wherein the plate body is deformable so that the plate body assumes a form with a decreased curvature when the spikes are in an engaging configuration.

4. The cranial plate according to claim 1, wherein the plate body is plastically deformable.

5. The cranial burr hole plate according to claim 1, wherein the plate body is elastically deformable.

6. The cranial plate according to claim 5, wherein the plate body has a bistable configuration and is configured to bias the spikes into the engaging configuration when elastically deformed.

7. The cranial plate according to claim 1, wherein at least one of the spikes is configured to contact a wall of a burr hole when the plurality of spikes is in the engaging configuration.

8. The cranial plate according to claim 1, wherein the circumferential ring is configured to contact a cranial bone surface.

9. The cranial plate according to claim 8, wherein the circumferential ring is configured to support at least a subset of the plurality of spikes.

10. The cranial plate according to claim 8, wherein the spikes extend from an inner rim of the circumferential ring.

11. The cranial plate according to claim 1, wherein the plate body comprises an alignment feature to align the plate body with a deformation instrument.

12. The cranial plate according to claim 11, wherein the alignment feature comprises at least one opening in the plate body for insertion of a portion of the deformation instrument.

13. The cranial plate according to claim 1, wherein the cranial plate is formed in one piece.

14. The cranial plate according to claim 1, wherein the plate body has a bone facing side, and wherein the plurality of spikes extends from the bone facing side of the plate body.

15. A deformation instrument for moving the spikes of a cranial plate comprising a plate body and a plurality of spikes extending from the plate body, into an engaging configuration upon deformation of the plate, the instrument comprising:
 a radially outer sleeve; and
 a radially inner stamp disposed inside the radially outer sleeve and axially movable thereto,
 wherein the stamp is configured to deform the plate upon application of an axial force on the stamp, and
 wherein the axial force is due to the axial movement of the radially inner stamp.

16. The deformation instrument according to claim 15, wherein the stamp comprises a first stamp portion and a second stamp portion, wherein the first stamp portion is concentric to the second stamp portion, and wherein the first stamp portion is configured to deform the plate body of the plate and the second stamp portion is configured to deform the plurality of spikes of the plate.

17. The deformation instrument according to claim 15, further comprising an alignment feature configured to engage a complementary alignment feature of the plate body.

18. A cranial plating system comprising:
 a cranial plate comprising:
 a plate body; and
 a plurality of spikes extending from the plate body, the spikes configured to engage cranial bone, wherein the plate is deformable to enable movement of the spikes from a disengaging configuration to an engaging configuration upon deformation of the plate; and
 a deformation instrument for moving the spikes of the cranial plate into the engaging configuration, the instrument comprising:
 a radially outer sleeve;
 a radially inner stamp disposed inside the radially outer sleeve and axially movable thereto,
 wherein the stamp is configured to deform the plate upon application of an axial force on the stamp, and
 wherein the axial force is due to the axial movement of the radially inner stamp.

19. A method for closing a cranial burr hole, comprising:
 placing a deformable plate onto the burr hole,
 wherein the plate comprises a plate body and a plurality of spikes extending from the plate body,
 wherein the plate body includes a circumferential ring, a central hub, and a plurality of spokes extending radially inward from the circumferential ring to the central hub; and
 deforming the plate to move the spikes from a disengaging configuration to an engaging configuration in which the spikes engage cranial bone,
 wherein when the plate is deformed the plurality of spikes are bent away from the central hub and toward the circumferential ring to move the plurality of spikes from the disengaging configuration to the engaging configuration.

20. The method according to claim 19, wherein the step of deforming the plate is performed by applying an axial force on the plate by a stamp of a deformation instrument.

\* \* \* \* \*